US005874145A

United States Patent [19]

Waller

[11] Patent Number: 5,874,145

[45] Date of Patent: Feb. 23, 1999

[54] IDENTIFICATION DOCUMENT WITH ENHANCED LEVEL OF SECURITY

[75] Inventor: Robert A. Waller, Rowlett, Tex.

[73] Assignee: E-Systems, Inc., Dallas, Tex.

[21] Appl. No.: 927,582

[22] Filed: Sep. 11, 1997

Related U.S. Application Data

[62] Division of Ser. No. 608,658, Feb. 29, 1996.

[51] Int. Cl.[6] .......... A61F 13/02

[52] U.S. Cl. .......... 428/42.1; 438/40.1; 438/41.7; 438/41.8; 438/42.2; 283/62; 283/109

[58] Field of Search .......... 283/81, 95, 98, 283/101, 103, 62, 109, 77, 82, 75, 112, 74, 6–9; 428/40–43

[56] References Cited

U.S. PATENT DOCUMENTS

| | | | |
|---|---|---|---|
| 382,726 | 8/1888 | McVoy et al. | 283/7 |
| 3,237,331 | 3/1966 | Gill, Jr. | 40/137 |
| 3,801,183 | 4/1974 | Sevelin et al. | 350/105 |
| 3,898,086 | 8/1975 | Franer et al. | 96/28 |
| 3,919,031 | 11/1975 | White | 156/219 |
| 4,099,838 | 7/1978 | Cook et al. | 350/105 |
| 4,184,701 | 1/1980 | Franklin et al. | 283/9 R |
| 4,287,285 | 9/1981 | Mosehauer | 430/124 |
| 4,298,217 | 11/1981 | Moraw et al. | 283/7 |
| 4,304,809 | 12/1981 | Moraw et al. | 428/195 |
| 4,322,461 | 3/1982 | Raphael et al. | 428/14 |
| 4,325,196 | 4/1982 | Gauch et al. | 40/2.2 |
| 4,370,397 | 1/1983 | Ceintrey et al. | 430/10 |
| 4,377,988 | 3/1983 | Tung et al. | 119/106 |
| 4,425,421 | 1/1984 | Rutges et al. | 430/238 |
| 4,464,454 | 8/1984 | Vogt | 430/256 |
| 4,467,335 | 8/1984 | Schmidt et al. | 346/160 |
| 4,496,618 | 1/1985 | Pernicano | 428/201 |
| 4,497,872 | 2/1985 | Hoppe et al. | 428/483 |
| 4,504,083 | 3/1985 | Devrient et al. | 283/77 |
| 4,507,346 | 3/1985 | Maurer et al. | 428/158 |
| 4,507,349 | 3/1985 | Fromson et al. | 428/195 |
| 4,511,908 | 4/1985 | Small | 346/206 |
| 4,519,155 | 5/1985 | Gallagher et al. | 40/625 |
| 4,519,632 | 5/1985 | Parkinson et al. | 283/75 |
| 4,523,777 | 6/1985 | Holbein et al. | 283/67 |
| 4,531,765 | 7/1985 | Shulman | 283/114 |
| 4,536,013 | 8/1985 | Haghiri-Therani et al. | 283/77 |
| 4,544,181 | 10/1985 | Maurer et al. | 283/74 |
| 4,560,426 | 12/1985 | Moraw et al. | 156/64 |
| 4,564,409 | 1/1986 | Kuhl | 156/219 |
| 4,579,754 | 4/1986 | Maurer et al. | 428/29 |
| 4,596,409 | 6/1986 | Holbein et al. | 283/75 |
| 4,629,215 | 12/1986 | Maurer et al. | 283/94 |
| 4,630,891 | 12/1986 | Li | 350/105 |
| 4,635,965 | 1/1987 | Vogt | 283/112 |
| 4,650,283 | 3/1987 | Orensteen et al. | 350/105 |
| 4,653,775 | 3/1987 | Raphael et al. | 283/108 |
| 4,663,518 | 5/1987 | Borror et al. | 235/487 |
| 4,673,626 | 6/1987 | Takeda et al. | 430/14 |
| 4,688,894 | 8/1987 | Hockert | 350/105 |
| 4,691,993 | 9/1987 | Porter et al. | 350/105 |

(List continued on next page.)

*Primary Examiner*—Merrick Dixon

*Attorney, Agent, or Firm*—Baker & Botts, L.L.P.

[57] ABSTRACT

An identification document and a method of placing personalized data (variable text and color image) directly on the identification document having a data receiving page. The method comprises the steps of: printing personalized data directly onto a silicone release coat of a release sheet; positioning the release sheet with the side containing fused toner adjacent to the adhesive of an adhesive side of a security laminate; passing the release sheet and the security laminate through a laminator to transfer the personalized data to the adhesive of the security laminate; removing the release sheet leaving the personalized data on the security laminate; and passing the security laminate and the data receiving page through a laminator to seal personalized data between the security laminate and the data receiving page.

5 Claims, 5 Drawing Sheets

U.S. PATENT DOCUMENTS

| | | | |
|---|---|---|---|
| 4,692,394 | 9/1987 | Drexler | 430/140 |
| 4,710,617 | 12/1987 | Mouchotte | 235/487 |
| 4,713,365 | 12/1987 | Harrison | 503/227 |
| 4,728,983 | 3/1988 | Zwadlo et al. | 355/4 |
| 4,732,410 | 3/1988 | Holbein et al. | 283/67 |
| 4,738,949 | 4/1988 | Sethi et al. | 503/227 |
| 4,748,452 | 5/1988 | Maurer | 346/1.1 |
| 4,763,985 | 8/1988 | Bingham | 350/105 |
| 4,765,656 | 8/1988 | Becker et al. | 283/70 |
| 4,766,026 | 8/1988 | Lass et al. | 428/203 |
| 4,808,509 | 2/1989 | Vervloet et al. | 430/237 |
| 4,824,142 | 4/1989 | Dossche | 282/11.5 |
| 4,869,941 | 9/1989 | Ohki | 428/40 |
| 4,889,749 | 12/1989 | Ohashi et al. | 428/13 |
| 4,894,110 | 1/1990 | Lass et al. | 156/272.8 |
| 4,896,943 | 1/1990 | Tolliver et al. | 350/105 |
| 4,911,478 | 3/1990 | Oshikoshi et al. | 283/109 |
| 4,928,996 | 5/1990 | Oshikoshi et al. | 283/109 |
| 4,968,063 | 11/1990 | McConville et al. | 283/72 |
| 4,988,126 | 1/1991 | Heckenkamp et al. | 283/92 |
| 4,992,353 | 2/1991 | Rodakis et al. | 430/213 |
| 5,002,312 | 3/1991 | Phillips et al. | 283/72 |
| 5,011,570 | 4/1991 | Ohbayashi | 156/310 |
| 5,080,463 | 1/1992 | Faykish et al. | 359/536 |
| 5,096,229 | 3/1992 | Carlson | 283/75 |
| 5,106,719 | 4/1992 | Oshikoshi et al. | 430/203 |
| 5,122,813 | 6/1992 | Lass et al. | 346/1.1 |
| 5,131,686 | 7/1992 | Carlson | 283/75 |
| 5,135,263 | 8/1992 | Terwel | 283/112 |
| 5,213,648 | 5/1993 | Vermeulen et al. | 156/307 |
| 5,219,183 | 6/1993 | McKillip | 283/62 |
| 5,244,234 | 9/1993 | Oshima et al. | 283/109 |
| 5,250,133 | 10/1993 | Kawamura et al. | 156/240 |
| 5,261,987 | 11/1993 | Luening et al. | 156/235 |
| 5,267,755 | 12/1993 | Yamauchi et al. | 283/86 |
| 5,310,222 | 5/1994 | Chatwin et al. | 283/86 |
| 5,324,567 | 6/1994 | Bratchley et al. | 428/195 |
| 5,350,198 | 9/1994 | Bernecker | 283/77 |
| 5,358,582 | 10/1994 | Koshizuka et al. | 156/235 |
| 5,366,833 | 11/1994 | Shaw et al. | 430/10 |
| 5,380,044 | 1/1995 | Aitkens et al. | 283/67 |
| 5,380,695 | 1/1995 | Chiang et al. | 503/227 |
| 5,387,013 | 2/1995 | Yamauchi et al. | 283/86 |
| 5,435,599 | 7/1995 | Bernecker | 283/70 |

IDENTIFICATION DOCUMENT WITH ENHANCED LEVEL OF SECURITY

This is a division of application Ser. No. 08/608,658 filed Feb. 29, 1996 pending.

TECHNICAL FIELD

This invention relates generally to identification documents and, more particularly, to identification documents and a method of placing personalized data (including text and image) in an identification document, such as a passport.

BACKGROUND OF THE INVENTION

There are usually two types of printing on identification cards and passports. The first type of printing involves background printing that includes reference and security information. For example, the reference information may include the issuing agency as well as numerical data. The security information may be in the form of a watermark, an encoded magnetic strip, numerical sequences, a holographic image, etc. The second type of printing includes "personalized data" or "variable information" such as photographic, fingerprint, signature, name, address, etc.

Personalized text and image data is placed into most current passports by printing text directly into the booklet on a data receiving page with a daisy wheel-like printer and then affixing a photograph of the passport holder to the data page. This produces a passport that is vulnerable to photo-substitution. According to many forensic experts, photo-substitution accounts for over seventy percent of the incidents of passport tampering and alteration. Recent improvements in digital printing technology offer a potential method for countering this photo-substitution threat. New digital full-color printers produce near photographic quality images and passports produced with this technology offer enhanced levels of security because the images are considerably more difficult to remove and alter as compared to the photograph counterpart.

Several means of placing the variable text and image data into the passport booklet have been proposed in the past few years. One technique is based on an insert page concept. A sheet of security paper such as that used to make currency or a special synthetic paper such as Teslin is preprinted with an appropriate passport security background. The finished sheet is die cut to the dimensions of the passport creating an insert data page. This data page is positioned into the passport and then attached to the booklet via a thermal lamination process. A security laminate, which is sewn into the booklet during the fabrication process, holds the data page in the document. While this technique does provide a method of placing the variable text and color image data into the passport, it also introduces a new point of vulnerability. The entire data page can be removed from the booklet by attacking the security laminate.

SUMMARY OF THE INVENTION

In accordance with the present invention, an identification document, e.g. a passport, is prepared by a method including printing personalized data directly onto a silicone release coat of the release sheet using a printer having a maximum and minimum fusing temperature, wherein the fusing temperature of the printer is controlled such that the maximum fusing temperature is below the point that the print toner will become brittle when the printed sheet is flexed and such that the minimum fusing temperature is above the point required to adequately fuse the toner to the silicon release coat. The release sheet is positioned with the side containing fused toner adjacent to the adhesive of a security laminate. Next, the release sheet and the security laminate are passed through a laminator thereby transferring the personalized data to the adhesive of the security laminate. Following lamination, the release sheet is removed leaving the personalized data on the security laminate.

The present invention offers enhanced levels of passport security over previous methods because all of the primary components of the document including the security laminate and the data receiving page are sewn into the passport booklet during fabrication rather than being inserted when the variable text and data are added. The overall security of the document is greatly enhanced because neither the laminate nor the data receiving page can be removed from the passport booklet without cutting.

BRIEF DESCRIPTION OF THE DRAWINGS

A more complete understanding of the present invention may be had by reference to the following Detailed Description when taken in conjunction with the accompanying drawings wherein.

DETAILED DESCRIPTION OF THE INVENTION

Figure 1:
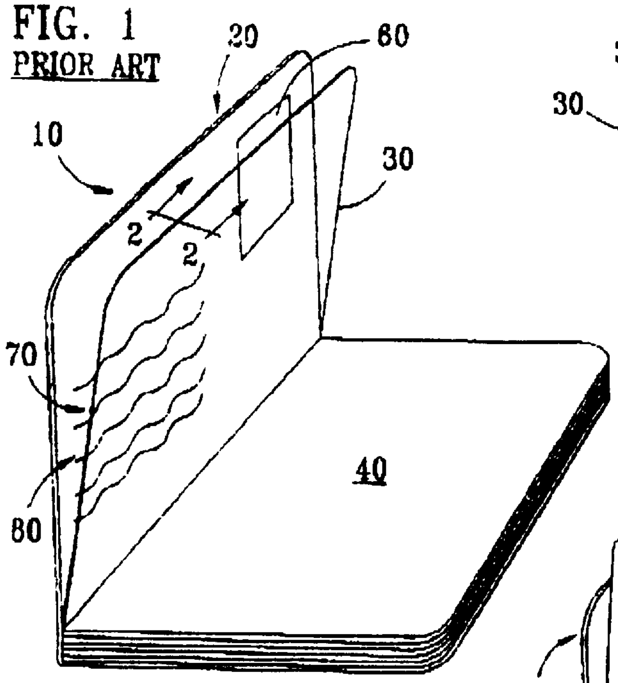
FIG. 1 PRIOR ART
FIG. 1 is a perspective view of a typical prior art passport booklet.
Figure 2:
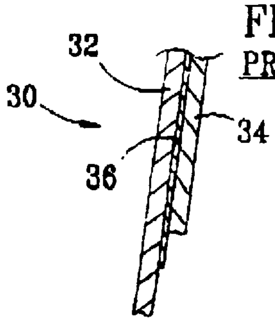
FIG. 2 PRIOR ART
FIG. 2 is an enlarged partial side view of a security laminate page of the prior art passport booklet of FIG. 1.

Reference is now made to the Drawings wherein like reference characters denote like or similar parts throughout the 13 FIGURES. Referring to FIG. 1, therein is illustrated a current typical passport booklet 10. The current passport 10 configuration includes a data receiving page 80, usually of security paper affixed to the inside of the front cover 20, a die cut photograph 60 affixed to the data receiving page 80 and the variable text data 70 printed directly onto the data receiving page 80. A security laminate 30 is sewn into the passport booklet 10 to protect the document against wear and information substitution. After printing personalized data on the data receiving page 80 and attaching the photograph 60 to the data receiving page 80, the security laminate 30 is sealed to the receiving page 80 by passing the passport booklet 10 through a passport laminator. FIG. 2 illustrates that the typical security laminate includes a first layer of polyethylene based adhesive 32, a polyester cover 34 and a primer interface 36.

Although the description of the invention will proceed to make reference to a passport booklet, it should be understood that the invention relates to identification documents and the method of making such documents.

Figure 3:
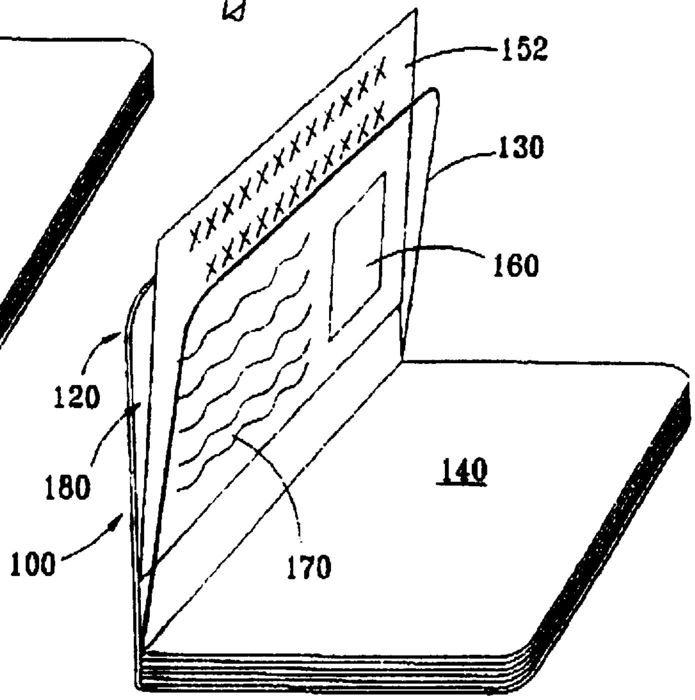
FIG. 3 is a perspective view an identification page of a passport booklet constructed according to a first embodiment of the present invention.

Referring now to FIG. 3, the present invention offers enhanced levels of security over other methods because all of the primary components of the passport booklet 100 including the security laminate 130 and the data receiving page 180 are sewn into the passport booklet during fabrication rather than being inserted when the personalized data is added. It is understood that sewing is not the only acceptable method of affixing the elements of the passport booklet 100, any method of affixing that provides a tamper resistant means preventing the removal or replacement of pages in the passport booklet 100 is satisfactory.

Figure 4:
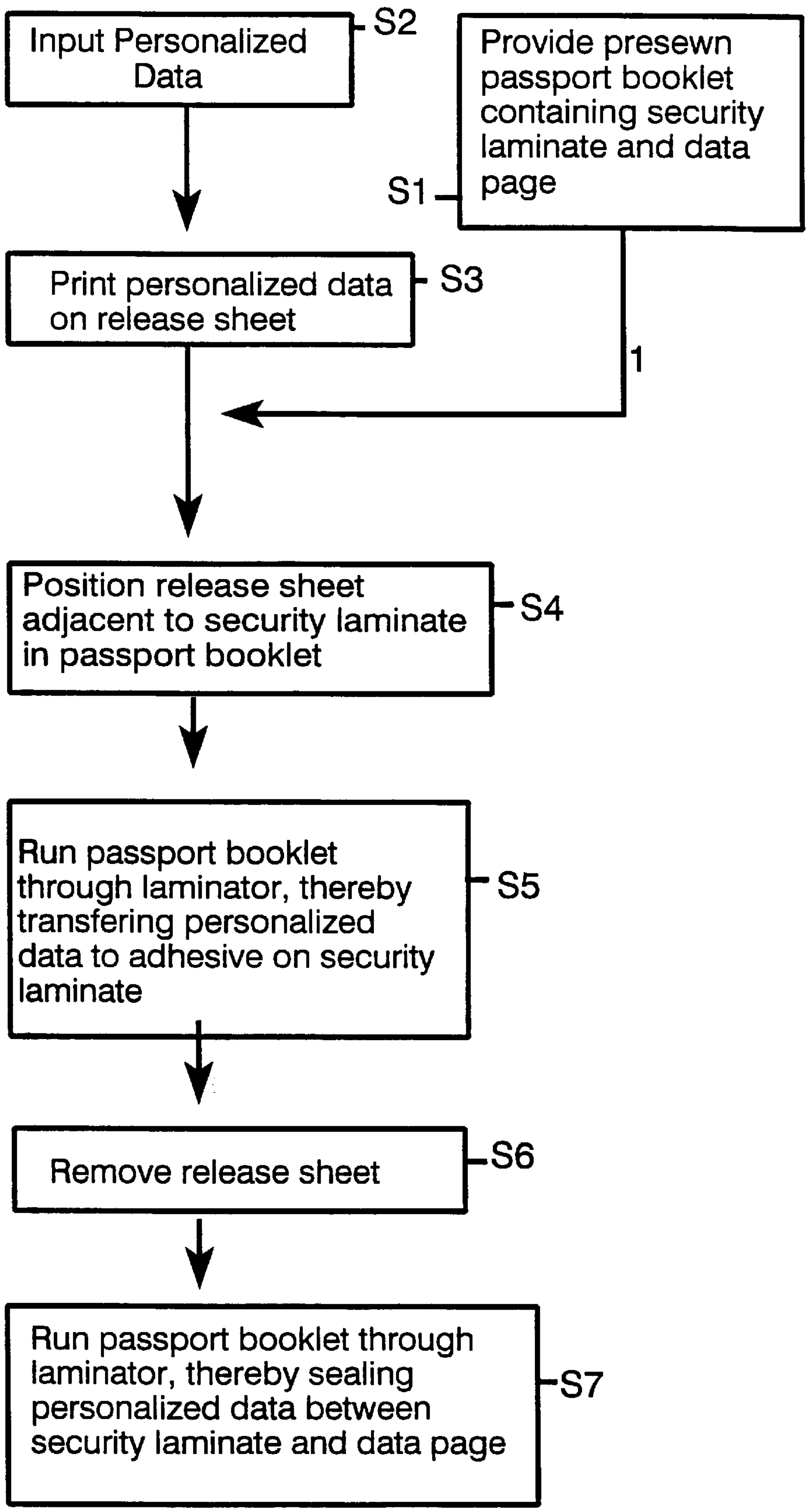
FIG. 4 is a flow chart showing the steps of the method of the present invention.

The steps employed in the method of the present invention are illustrated in FIG. 4 and described as follows. The presewn passport booklet 100 herein described above and illustrated in FIG. 3 is provided in Step S1. In the Step S2, formatted personalized data to be included in our identification page is input to a computer by various methods including using a scanning CCD array to read a signature or fingerprints, a computer keyboard for textual data, a scanner for scanning a photograph, using a frame grabber and video camera, and/or a digital camera. The data is digitized and downloaded to a printer.

Figure 5:
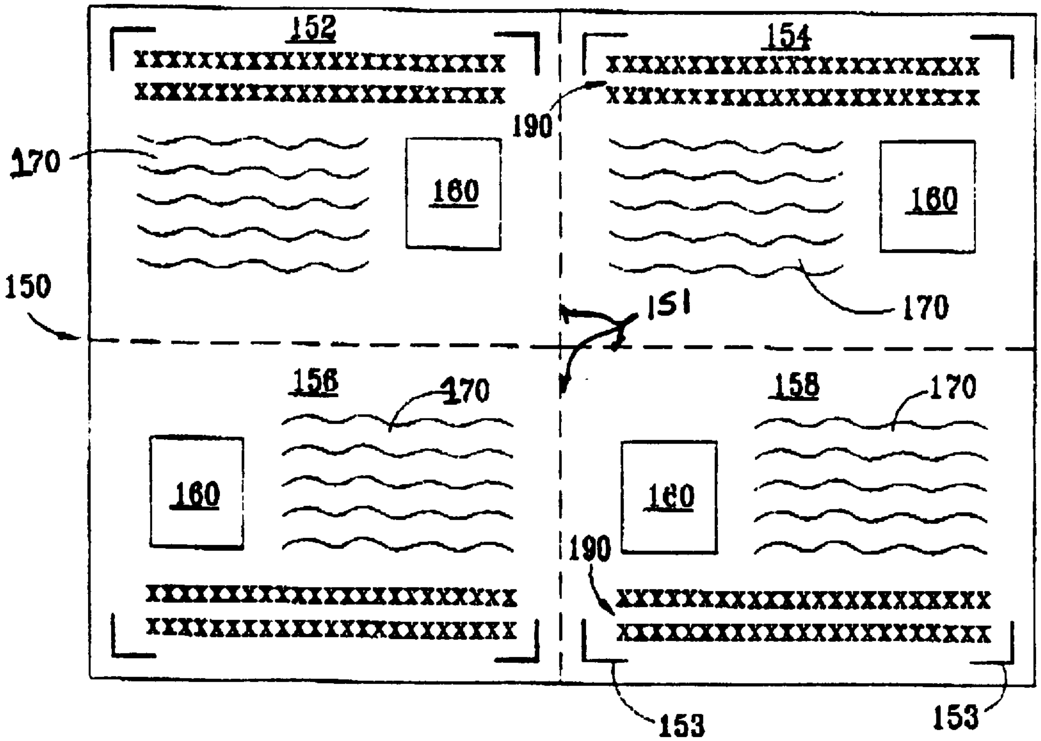
FIG. 5 is a plan view of a release sheet of the present invention after printing with personalized data for four separate individuals.

The personalized data is printed during Step S3 directly on a silicone release coat of a release sheet 150 (see FIG. 5). In one embodiment of the present invention, a black and white laser printer, such as the Hewlett-Packard Laserjet 4, was used to print black text and gray-scaled images while a color laser printer, such as the Ricoh NC5006, was used to print colored text and images. The Ricoh NC5006 prints color images and data directly onto the silicon release coat at the normal fuser roller pressures but improved quality images are achieved by slightly reducing the fuser roller temperature. Normal fusing temperatures cause the color laser toner to become brittle after fusing. This means that the toner will crack when the printed sheet is bent or flexed.

The best results to date have been achieved with a WC-40 STICK-NOTT™ S-Premium silicon release sheet manufactured by Release International with a basis weight of 40.0 lbs./ream. The technical data for this release paper is provided below:

PHYSICAL TEST DATA (Typical Average Values)

| Characteristic | Test Method | Nominal Value | Nominal Value |
|---|---|---|---|
| Release (12"/min) | UM-502 | 5015 gm/in | 5–15 gm/25 mm |
| (1200"/min) | | 60–90 gm/in | 60–90 gm/25 mm |
| Basis Weight | TAPPI T-410 | 40.0 lbs/ream | 65 g/m$^2$ |
| Caliper | TAPPI T-411 | 2.75 mils | 70 microns |
| Tear Strength CD | TAPPI T-414 | 53 grams | 53 grams |
| Tensile Strength MD | TAPPI T-404 | 23 lbs/in | 4.0 kN/m |
| Brightness | TAPPI T-452 | 82.0 nm | 82.0 nm |
| MG Sheffield Smoothness | UM-518 | 2.75 SFU | 2.75 SFU |

The best quality color images were achieved with this release sheet by reducing the fuser roller temperature to ~150° C. on the Ricoh NC5006 printer. Fusing temperatures that are too high will cause the toner to become brittle and crack when the sheet is flexed and temperatures that are too low do not adequately fuse the color toner to the release surface. However, at the proper fuser roller temperature setting, the fused information can be touched and lightly rubbed without smearing or destroying the text or images. The proper fuser temperature setting is dependent upon the thermal mass and, therefore, the basis weight of the release sheet.

FIG. 5 illustrates an example configuration of a printed silicon release sheet 150 showing the layout of the variable text and image data. In this configuration, the release sheet 150 is standard letter size of 8½"×11". This size is adequate to produce four individual passport documents 152, 154, 156, 158. The sheet 150 has perforated lines 151 so that it can be easily torn into the four equal quadrants 152, 154, 156, and 158 after the printing process. Personalized data including photographic image 160, textual image 170 and OCR-B machine readable text 190 are illustrated as printed on the release sheet.

Returning to FIGS. 3 and 4 in Step S4, one of the quarter sheets, for illustrative purposes sheet 152, is placed between the data receiving sheet 180 and the security laminate 130. The security laminate 130 is positioned so that the adhesive side faces the data receiving page 180. The release sheet 152 is positioned so that the personalized information is facing the adhesive side of the security laminate 130.

Figure 6:
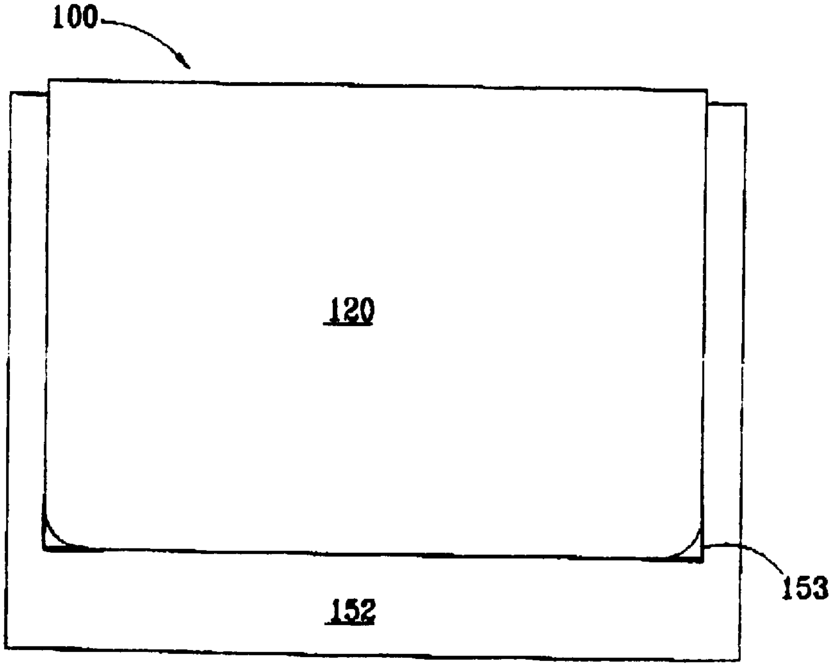
FIG. 6 is a plan view showing an alignment of the release sheet just prior to transfer of personalized information to the identification page.

Referring to FIGS. 5 and 6, alignment guides 153 are printed on each quarter sheet so that the text data 170 and image data 160 are positioned properly relative to the edges of the passport booklet 100.

The release sheet 150, including security laminate 130, are passed during Step S5 through a conventional laminator such as a 1000PLA from Thermal Laminating Corporation. The heaters are gapped to the approximate thickness of the passport booklet 100 and the temperature is adjusted to an interface temperature of 125° C. for typical polyethylene-based adhesives. The required interface temperature is dependent upon the adhesive formulation. The corresponding temperature setting on the laminator is dependent upon the thermal mass of the passport booklet 100 and, therefore, the thickness of the passport booklet 100 as well as the speed of the laminator. The laminator transfers the personalized data from the release sheet 150 to the adhesive of the adjacent security laminate 130. The personalized data including image and all of the text is transferred to the adhesive in a single pass rather than being printed directly to the laminate via a three-color or four-color print process.

While the donor release sheet 150 and security laminate 130 are still hot from the initial pass through the laminator, the release sheet 150 is peeled in Step S6 from the security laminate 130 and discarded.

After the image transfer is completed and the release sheet 150 is removed from the document, the passport booklet 100 is sent through the passport laminator a second time in Step S7 to seal the security laminate 130 to the data receiving page 180. In this embodiment, the data receiving page 180 is attached to the inside of the cover 120.

It is to be understood that the data receiving page 180 represents an identification document and may not be located in the passport booklet 100. Additionally, the data receiving page 180 may be a completely blank security coded paper or contain preprinted standard form information, leaving only blank space for the personalized data to be affixed. If the data receiving page is completely blank then the standard form information is downloaded to the printer concurrently with the personalized data and affixed concurrently as heretofore described with regard to the personalized data.

The method of the present invention is applicable to plain polyethylene hot melt adhesive as well as a number of copolymers including EAA (ethylene/acrylic acid copolymer), EEA (ethylene/ethyl acrylate copolymer), EMA (ethylene/acrylate copolymer), and EVA (ethylene/vinyl acetate copolymer). Furthermore, the process is not limited to hot melt adhesive applications. The transfer process can be used with pressure sensitive adhesives (PSA).

Figure 7:
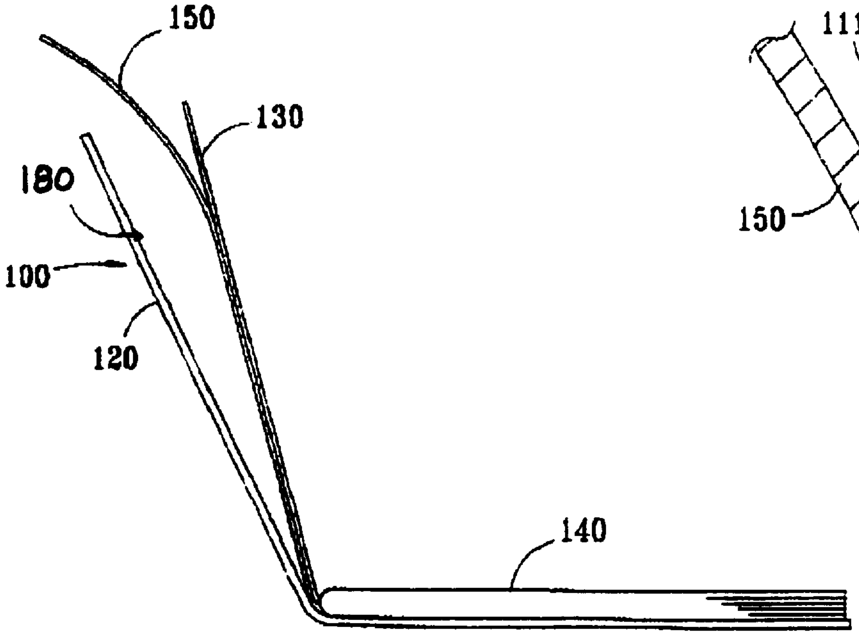
FIG. 7 is a side view of the identification page of the passport booklet of FIG. 3.
Figure 8:
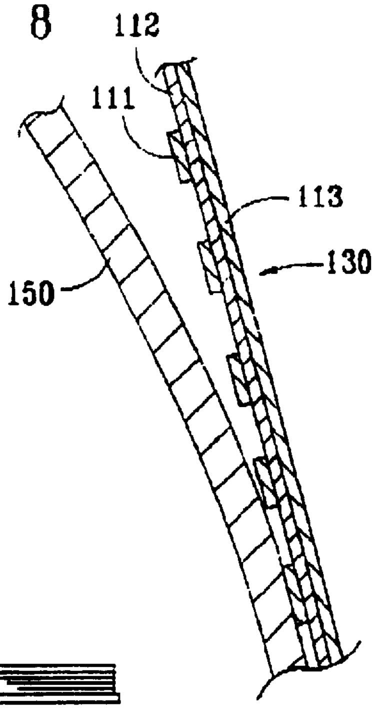
FIG. 8 is an enlarged partial side view of a security laminate identification page of the passport booklet of FIG. 3.

FIGS. 7–11 illustrate cross sections of various possible identification document configurations. FIGS. 7 and 8 illustrate the configuration as previously described with regard to FIG. 3, just prior to the final lamination Step S7. FIGS. 7 and 8 illustrate the process as the silicon-coated release sheet 150 is removed from the security laminate 130. The final configuration of this example will result in the security laminate 130 being affixed to the data receiving page 180 that is affixed to the inside of the front cover 120.

FIG. 8 illustrates the silicon coated release sheet 150, printer toner 111 (consisting of approximately 90–95% polyester and 5–10% pigment), a polyethylene based copolymer adhesive 112, and a polyester security laminate cover 113.

Figure 9:
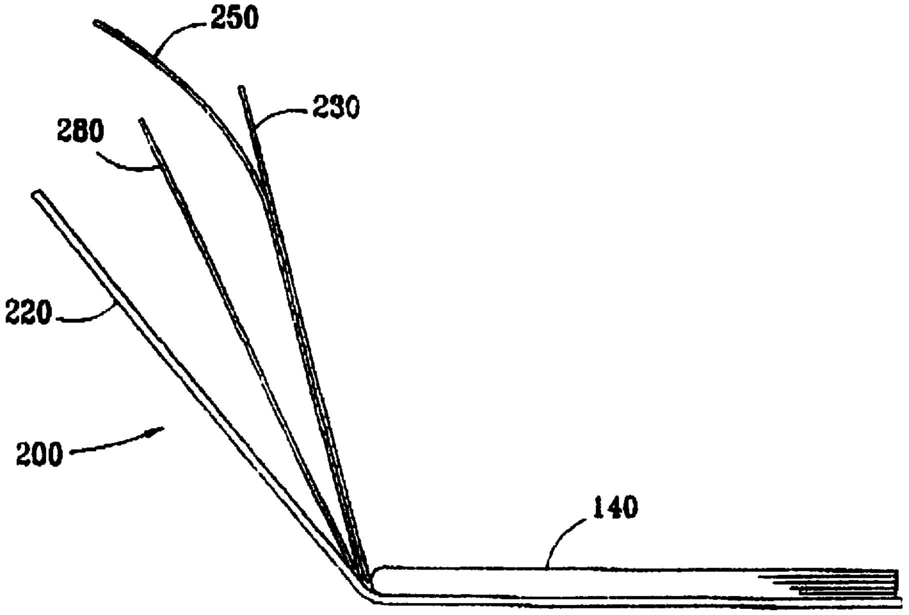
FIG. 9 is a side view of a passport booklet constructed according to a second embodiment of the method of the present invention.

FIG. 9 illustrates a second embodiment of the present invention, depicted at the same stage of the assembly as shown in FIGS. 7 and 8. In this configuration, the security laminate 230 is sealed to an inner data receiving page 280 not affixed to the inside of the front cover 220 of the passport booklet 200. The location and side orientation of the data page 280 is determined by the placement of the security laminate 230 during the fabrication process.

Figure 10:
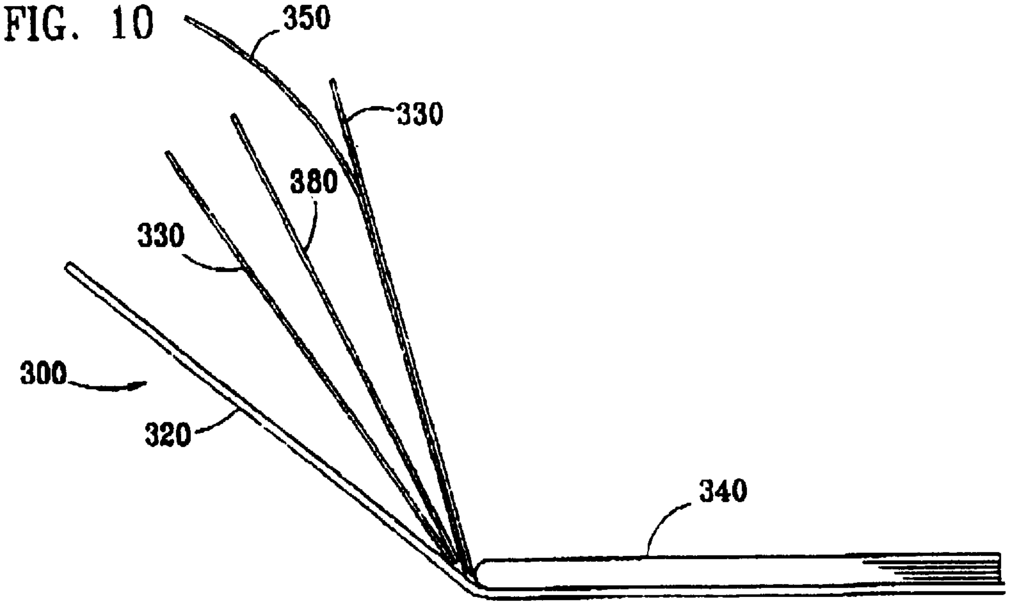
FIG. 10 is a side view of a passport booklet constructed according to a third embodiment of the method of the present invention.

FIG. 10 illustrates a third embodiment of the present invention. In this embodiment, the data page 380 is sealed between two opposing layers of security laminates 330. Again, the location and side orientation of the data receiving page 380 is determined by the placement of the security laminates 330 during the fabrication.

Figure 11:
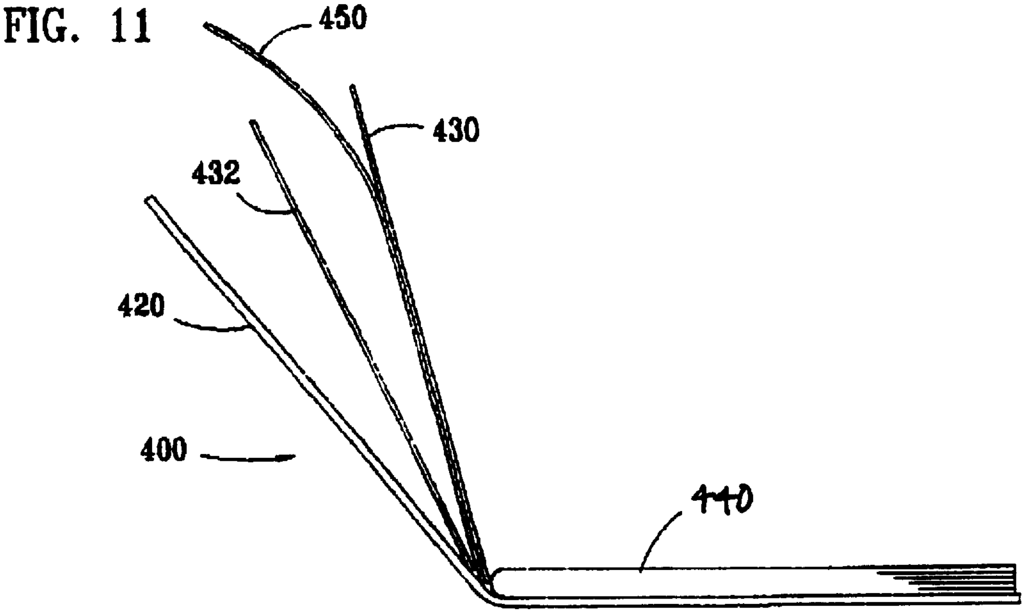
FIG. 11 is a side view of a passport booklet constructed according to a fourth embodiment of the method of the present invention.

A fourth embodiment is illustrated in FIG. 11. This embodiment does not utilize a data receiving page. Instead, the personalized data is transferred to a first security laminate 430 and then is sealed to a second security laminate 432. The personalized data is held in place between layers of adhesive of the opposing layers of security laminate 430 and 432.

Figure 13:
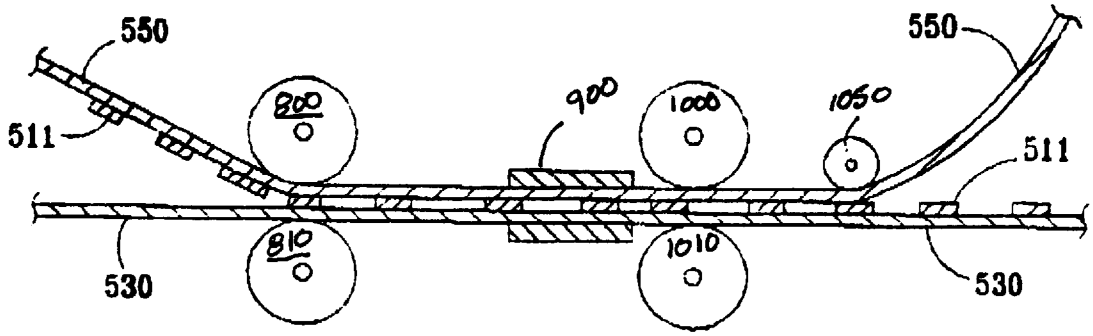
FIG. 13 is a side view of an apparatus for transferring personalized data to a vinyl substrate according to the present invention.
Figure 12:
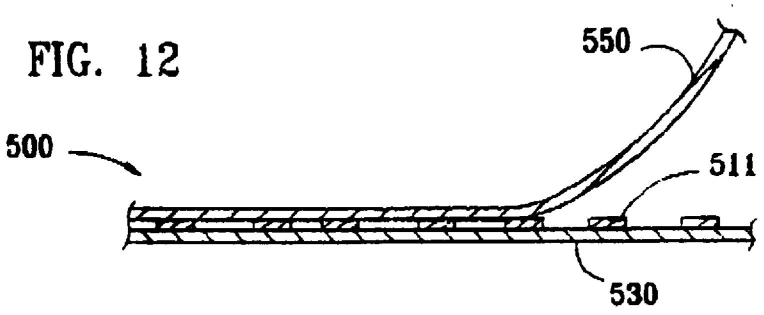
FIG. 12 is a side view of an alternative use of the present invention to print personalized data on a vinyl substrate.

Referring to FIGS. 12 and 13, the invention, as explained, is applicable to identification documents 500. The personalized data associated with an identification document is printed in reverse onto sheets of the silicon-coated release material 550. The printed release sheet 550 is placed on a vinyl based substrate 530 and passed through a laminator at an interface temperature of 125°–150° C. When the release sheet 550 is peeled away from the vinyl substrate 530, laser printer toner 511 (comprising 90–95% polyester and 5 to 10 pigment is left on the vinyl substrate), thereby the personalized image is transferred to the substrate 530. The process has been demonstrated on release sheets 550 as large as 11"×17" which will accommodate 18–21 identification documents.

Apparatus for transferring personalized data to vinyl substrates is shown FIG. 13. A silicon coated donor release sheet 550 having personalized data printed in reverse is fed through rollers 800 and 810. Heat is applied by a heater 900 and pressure is applied by compression rollers 1000 and 1010. The release sheet 550 is removed from the vinyl substrate 530 by stripper rollers 1050, leaving the personalized data in a transfer positive image 511 on the vinyl substrate 530.

Although the preferred and alternative embodiments of the invention have been illustrated in the accompanying Drawings and described in the foregoing Detailed Description, it will be understood that the invention is not limited to the embodiment disclosed but is capable of numerous modifications without departing from the scope of the invention as claimed.

I claim:

1. An identification document having an enhanced level of security, comprising:

a security laminate having an adhesive surface and personalized data transferred thereto in the form of a fused toner on the adhesive surface; and a data receiving sheet positioned against the adhesive surface containing the personalized data of the security laminate, wherein said data receiving sheet and the security laminate are laminated together thereby substantially securing the personalized data against tampering.

2. An identification document having an enhanced level of security as set forth in claim 1 including a passport booklet attached to the laminated data receiving sheet and the security laminate.

3. An identification document having an enhanced level of security as set forth in claim 1 further comprising a second security laminate having an adhesive surface and personalized data transferred thereto in a form of a fused toner on the adhesive surface, wherein the data receiving sheet is positioned against the adhesive surface containing the personalized data of the second security laminate and laminated thereto thereby substantially securing the personalized data on the adhesive surface of the second laminate against tampering.

4. An identification document having an enhanced level of security, comprises:

a first security laminate having an adhesive surface and personalized data transferred thereto in the form of a fused toner on the adhesive surface; and a second security laminate having an adhesive surface positioned against the adhesive surface containing the personalized data of the first security laminate, wherein said first security laminate and the second security laminate are laminated together thereby substantially securing the personalized data against tampering.

5. An identification document having an enhanced level of security as set forth in claim 4 further comprising a passport booklet attached to the laminated first security laminate and second security laminate.

* * * * *